(12) United States Patent
Bonnamy et al.

(10) Patent No.: US 9,050,260 B2
(45) Date of Patent: Jun. 9, 2015

(54) COSMETIC COMPOSITION COMPRISING AT LEAST ONE SILICONE COPOLYMER AND AT LEAST ONE LIQUID VOLATILE LINEAR ALKANE MIXTURE

(75) Inventors: Arnaud Bonnamy, Versailles (FR); Gaëlle Brun, Paris (FR)

(73) Assignee: L'OREAL, Paris (FR)

( * ) Notice: Subject to any disclaimer, the term of this patent is extended or adjusted under 35 U.S.C. 154(b) by 366 days.

(21) Appl. No.: 12/855,425

(22) Filed: Aug. 12, 2010

(65) Prior Publication Data

US 2011/0139171 A1    Jun. 16, 2011

Related U.S. Application Data

(60) Provisional application No. 61/235,108, filed on Aug. 19, 2009.

(30) Foreign Application Priority Data

Aug. 13, 2009   (FR) ..................... 09 55660

(51) Int. Cl.
| | | |
|---|---|---|
| *A61K 8/58* | (2006.01) | |
| *A61K 8/00* | (2006.01) | |
| *A61K 8/31* | (2006.01) | |
| *A61K 8/891* | (2006.01) | |
| *A61Q 5/12* | (2006.01) | |
| *A61Q 5/06* | (2006.01) | |

(52) U.S. Cl.
CPC . *A61K 8/31* (2013.01); *A61K 8/891* (2013.01); *A61Q 5/12* (2013.01); *A61Q 5/065* (2013.01)

(58) Field of Classification Search
CPC ....... A61K 8/31; A61K 8/585; A61K 8/8147; A61K 8/891; A61K 8/892; A61K 2800/544; A61K 8/817; A61K 8/89; A61K 8/898; A61Q 1/06; A61Q 5/065; A61Q 1/04; A61Q 5/12; A61Q 5/06; A61Q 5/10
USPC .......................................... 424/70.121; 8/405
See application file for complete search history.

(56) References Cited

U.S. PATENT DOCUMENTS

| | | | |
|---|---|---|---|
| 4,374,825 A | * | 2/1983 | Bolich et al. ............... 424/70.12 |
| 6,280,851 B1 | | 8/2001 | Pasternack et al. |
| 2008/0269352 A1 | * | 10/2008 | Falkowski et al. ............ 514/762 |
| 2009/0053159 A1 | | 2/2009 | Brun |

FOREIGN PATENT DOCUMENTS

| | | | | |
|---|---|---|---|---|
| DE | 10 2008 012457 | | 12/2008 | |
| EP | 0 903 388 | | 3/1999 | |
| EP | 2 016 933 | | 1/2009 | |
| WO | WO 2004/073626 | | 9/2004 | |
| WO | WO 2010 003814 A1 | * | 1/2010 | ............... A61K 8/04 |

OTHER PUBLICATIONS

English language Abstract of DE 10 2008 012457, dated Dec. 24, 2008.
French Search Report for FR 09/55660, dated Apr. 23, 2010.

* cited by examiner

*Primary Examiner* — Aradhana Sasan
(74) *Attorney, Agent, or Firm* — The Marbury Law Group, PLLC

(57) ABSTRACT

Provided herein is a composition for treating keratin fibers that comprises at least one silicone copolymer based on at least one silicone resin and at least one fluid silicone, and at least one liquid volatile linear alkanes. Also provided herein is a method of treating keratin fibers, comprising applying the composition to the keratin fibers.

11 Claims, No Drawings

COSMETIC COMPOSITION COMPRISING AT LEAST ONE SILICONE COPOLYMER AND AT LEAST ONE LIQUID VOLATILE LINEAR ALKANE MIXTURE

This application claims benefit of U.S. Provisional Application No. 61/235,108, filed Aug. 19, 2009. This application also claims benefit of priority under 35 U.S.C. §119 to French Patent Application No. 0955660, filed Aug. 13, 2009.

Disclosed herein is a composition for treating keratin fibers, and, for example, human keratin fibers such as the hair, and a method of treating keratin fibers comprising applying this composition to the keratin fibers.

There can be numerous styling products that may provide the hair with body, mass or volume. One disadvantage associated with these products, which are usually based on film-forming polymers, may lie in the fact that the cosmetic effect can disappear at the first shampooing.

It may be known practice to coat the hair with film-forming polymers such as certain silicone copolymers based on silicone resin and fluid silicone, such as copolymers under the name BioPSA. These copolymers are described, for example, in International Application Publication Nos. WO 03/026596, WO 2004/073626, WO 2007/051505 and WO 2007/051506, for various cosmetic applications such as application to the hair, nails and skin.

This type of copolymer can be used to provide durable styling. When these copolymers are applied to the hair in a volatile solvent, the individual hairs can generally be coated homogeneously while remaining separated, and the coating obtained can generally be resistant to shampooing. This coating may provide the hair with body and mass in a durable way.

When these copolymers are used in a mixture with pigments, a visible coloring can be generally obtained, independently of the initial colour of the hair. This can be achieved, moreover, without prior bleaching of the hair. The presence of these pigments, such as nacres, may produce a visible chromatic coloring on hair. The coating obtained can be resistant to several shampooings.

The use of these copolymers is disclosed, for example, in document EP 2016933.

However, for good cosmetic and/or homogeneity properties on the part of the resultant coating, the rate of evaporation of the composition can be a key step. The rate of evaporation should not be too rapid, otherwise the composition may not spread well along the lock and the coating may not form homogeneously, a phenomena which can be manifested, for example, in increased difficulty in blow drying. The rate of evaporation should not be too slow, otherwise solvent may remain trapped in the coating after the drying step, and this can be detrimental to the cosmetic qualities of the coating. The volatile oils, such as isododecane, which are commonly used with copolymers based on silicone resin and fluid silicone have a rate of evaporation which can be too high. Moreover, it is always useful to obtain coating compositions which can produce further enhanced durability.

Accordingly, disclosed herein are homogeneous coatings resulting from compositions comprising solvents that have a rate of evaporation which can be appropriate for hair coating.

Also provided herein is a composition for treating keratin fibers, comprising at least one silicone copolymer based on at least one silicone resin and at least one fluid silicone, and at least one liquid volatile linear alkane comprising from 9 to 15 carbon atoms, wherein the weight ratio of the at least one liquid volatile linear alkane to the at least one silicone copolymer has a value greater than or equal to 2. Also provided is a method of treating keratin fibers, comprising applying this composition to the keratin fibers.

The use of the at least one liquid volatile linear alkane in combination with the at least one silicone copolymer as described above can make it possible to optimize the rate of evaporation, thereby facilitating the application of the composition and/or ensuring good homogeneity of the coating on the hair.

This method, when employed with a composition comprising at least one pigment, may produce homogeneous coatings having an intense and/or chromatic coloring, for example, on dark keratin fibers.

According to at least one embodiment, dark keratin fibers or hair may have a tone level lower than or equal to 6 (dark blonde) and, for example, lower than or equal to 4 (chestnut).

The term "tone level" is based on the classification of natural shades, one tone separating each shade from that immediately following or preceding it. This definition, and the classification of the natural shades, may be well known to styling professionals and are published in the book "Sciences des traitements capillaires" by Charles Zviak, 1988, published by Masson, pp. 215 and 278.

The tone levels run from 1 (black) to 10 (light light blonde), with one unit corresponding to one tone; the higher the number, the lighter the shade.

Copolymer Based on Silicone Resin and on Fluid Silicone

The at least one silicone copolymer disclosed herein is derived from the reaction between at least one silicone resin and at least one fluid silicone.

Such silicone copolymers may be described, for example, in "Silicone Pressure Sensitive Adhesives", *Sobieski and Tangney*, Handbook of Pressure Sensitive Adhesive Technology (D. Satas, Ed.), Van Nostrand Reinhold, New York.

According to at least one embodiment, the at least one silicone resin is present in a total amount ranging from 45% and 75% by weight, relative to the total weight of the at least one silicone copolymer and the at least one fluid silicone is present in a total amount ranging from 25% to 55% by weight relative to the total weight of the at least one silicone copolymer, with the sum of the percentages of the at least one silicone resin and of the at least one fluid silicone being equal to 100. For example, the at least one silicone resin can be present in a total amount ranging from 55% to 65% by weight, relative to the total weight of the at least one silicone copolymer and the at least one fluid silicone can be present in a total amount ranging from 35% to 45% by weight, relative to the total weight of the at least one silicone copolymer, with the sum of the percentages of the at least one silicone resin and of the at least one fluid silicone being equal to 100.

According to at least one embodiment, the at least one silicone resin disclosed herein is the product of condensation of groups $SiO_2$ and of groups $R_3(SiO)_{1/2}$ (triorganosilyl) in which each group R is independently chosen from methyl, ethyl, propyl and vinyl radicals and the ratio of the $SiO_2$ functions to the $R_3(SiO)_{1/2}$ functions of the at least one silicone resin ranges from 0.6:1 to 0.9:1. Triorganosilyl groups that may be used to form the at least one silicone resin may be chosen from trimethylsilyl, triethylsilyl, methylmethylpropylsilyl, dimethylvinylsilyl units, and mixtures thereof. According to at least one embodiment, trimethylsilyl groups are used to form the at least one silicone resin.

According to at least one embodiment, the at least one fluid silicone disclosed herein is a diorganopolysiloxane bearing OH end functions, having a viscosity ranging from 100 to 100,000 cSt at 25° C., in which the substituents of the diorganopolysiloxane are independently chosen from methyl, ethyl, propyl and vinyl radicals. According to at least one embodiment, the diorganopolysiloxanes are linear polymers. Examples of diorganopolysiloxanes may be, in a non-limiting manner, a polydimethylsiloxane, an ethylmethyl polysiloxane, a copolymer of dimethylsiloxane and of methylvinylsiloxane, and mixtures of such polymers or copolymers containing OH end groups. According to at least one embodiment, the diorganopolysiloxane is a polydimethylsiloxane.

Examples of synthesis of the at least one silicone copolymer are described, for example, in U.S. Pat. No. 5,162,410 or in CA 711 756.

The at least one silicone copolymer disclosed herein may thus be prepared by heating the following mixture:

at least one silicone resin in a total amount ranging from 45% to 75% by weight of the total weight of the at least one silicone copolymer, wherein the at least one silicone resin is the product of condensation of $SiO_2$ and $R_3(SiO)_{1/2}$ units in which each group R is independently chosen from methyl, ethyl, propyl and vinyl radicals and the ratio of the $SiO_2$ functions to the $R_3(SiO)_{1/2}$ functions of the at least one silicone resin ranges from 0.6:1 to 0.9:1;

at least one fluid diorganopolysiloxane containing OH end functions in a total amount ranging from 25% to 55% by weight of the at least one silicone copolymer, wherein the at least one fluid diorganopolysiloxane has a viscosity ranging from 100 to 100,000 cSt at 25° C., in which the substituents of the diorganopolysiloxane are independently chosen from methyl, ethyl, propyl and vinyl radicals; and at least one suitable catalyst in a total amount ranging from 0.001% to 5% by weight relative to the total weight of the at least one silicone copolymer, which can be an organic aliphatic amine compound, for example, chosen from primary amines, secondary amines, tertiary amines, carboxylic acid salts of the amines mentioned above and quaternary ammonium salts.

The above mixture is heated to a temperature ranging from 80° C. to 160° C. until the adhesive nature of the resulting silicone copolymer can be obtained.

According to at least one embodiment, the at least one silicone copolymer disclosed herein is sold by Dow Corning under the reference BIO-PSA®, these BIO-PSA® copolymers possibly being in two forms, standard or amine-compatible, and being provided in different solvents with a number of different silicone resin/fluid silicone ratios. Non-limiting mention may be made of the grades 7-4400, 7-4500 and 7-4600. According to at least one embodiment, the BIO-PSA® disclosed herein is the grade 7-4400.

According to at least one embodiment, the at least one silicone copolymer is present in a total amount of greater than 1% by weight of the total weight of the composition.

According to at least one embodiment, the at least one silicone copolymer may be present in the composition in a total amount of greater than 1% and up to 80% by weight, such as ranging from 1.5% to 40% by weight and further such as ranging from 1.5% to 20% by weight, relative to the total weight of the composition.

Volatile Linear Alkanes

According to at least one embodiment, the at least one volatile linear alkane disclosed herein may have a flash point in the range from 30 to 120° C., and, for example, from 40 to 100° C.

The at least one volatile linear alkane disclosed herein is liquid at ambient temperature (approximately 25° C.) and at atmospheric pressure (760 mmHg).

According to at least one embodiment, the at least one alkane disclosed herein may be a volatile linear alkane comprising from 9 to 15 carbon atoms, such as from 10 to 15 carbon atoms, and further such as from 11 to 14 carbon atoms.

According to at least one embodiment, the at least one volatile linear alkane disclosed herein may be of plant origin.

The at least one alkane of this kind may be obtained, directly or in two or more steps, from a plant raw material such as an oil, butter, wax, etc.

Non-limiting examples of alkanes appropriate for the compositions disclosed herein include the alkanes described in the International Application Publication Nos. WO 2007/068371, or WO 2008/155059, (mixtures of different alkanes differing by at least one carbon), by the company Cognis. These alkanes can be obtained from fatty alcohols, which can be themselves obtained from coconut oil or palm oil.

Non-limiting examples of the at least one volatile linear alkane disclosed herein include n-nonane (C9), n-decane (C10), n-undecane (C11), n-dodecane (C12), n-tridecane (C13), n-tetradecane (C14), n-pentadecane (C15), and mixtures thereof, and for example, the mixture of n-undecane (C11) and n-tridecane (C13), described in Example 1 of WO 2008/155059, and the mixture of n-dodecane (C12) and n-tetradecane (C14), sold by Sasol, under the names PARAFOL 12-97 and PARAFOL 14-97, which are linear dodecane and linear tetradecane, respectively, and also mixtures thereof.

It will be possible to use the volatile linear alkane alone or in a mixture of at least two separate volatile alkanes which differ from one another by a carbon number of at least 1.

According to at least one embodiment, a mixture is used of at least two separate volatile linear alkanes comprising from 10 to 15 carbon atoms and differing from one another by a carbon number of at least 1. Non-limiting examples include the volatile linear alkane mixtures C10/C11, C11/C12, C12/C13, or C14/C15.

According to at least one embodiment, a mixture is used of at least two separate volatile linear alkanes comprising from 10 to 15 carbon atoms and differing from one another by a carbon number of at least 2. Non-limiting examples include the volatile linear alkane mixtures C10/C12, or C12/C14, for an even carbon number n, and the mixtures C11/C13, or C13/C15, for an odd carbon number n.

According to at least one embodiment, a mixture is used of at least two separate volatile linear alkanes comprising from 10 to 15 carbon atoms which are separate and differ from one another by a carbon number of at least 2, and, for example, a mixture of C11/C13 volatile linear alkanes or a mixture of C12/C14 volatile linear alkanes.

According to at least one embodiment, other mixtures of more than two volatile linear alkanes, for example, a mixture of at least 3 volatile linear alkanes comprising from 9 to 15 carbon atoms which are separate and differ from one another by a carbon number of at least 1, can also be used, wherein the total amount of the volatile linear alkanes is more than 95% and for example more than 99% by weight of the total weight of the mixture.

According to at least one embodiment, in a mixture of volatile linear alkanes, the volatile linear alkane having the smallest carbon number is predominant in the mixture.

Non-limiting examples of mixtures of volatile linear alkanes disclosed herein include the following mixtures:

from 50% to 90% by weight, such as from 55% to 80% by weight, further such as from 60% to 75% by weight of the total weight of the mixture, of a volatile linear alkane comprising a carbon number of n, and from 10% to 50% by weight, such as from 20% to 45% by weight, further such as from 24% to 40% by weight of the total weight of the mixture, of a volatile linear alkane comprising a carbon number of n+x, with x greater than or equal to 1, for example, x=1 or x=2.

According to at least one embodiment, the mixture of volatile linear alkanes disclosed herein comprises:

less than 2% by weight, such as less than 1% by weight, of branched alkanes, and/or less than 2% by weight, such as less than 1% by weight, of aromatics, and/or less than 2% by weight, such as less than 1% by weight, and further such as less than 0.1% by weight, of alkenes and/or alkynes, in the mixture.

According to at least one embodiment, the at least one volatile linear alkane disclosed herein may be an n-undecane/n-tridecane mixture.

According to at least one embodiment, the at least one volatile linear alkane can be a mixture of volatile linear alkanes comprising:

from 55% to 80% by weight, such as from 60% to 75% by weight, of C11 volatile linear alkane (n-undecane), and from 20% to 45% by weight, such as from 24% to 40% by weight, of C13 volatile linear alkane (n-tridecane), relative to the total weight of the mixture.

According to at least one embodiment, the mixture of volatile linear alkanes is an n-undecane/n-tridecane mixture. Such a mixture may be obtained, for example, in accordance with Example 1 or Example 2 of WO 2008/155059.

According to at least one embodiment, the at least one volatile linear alkane disclosed herein may be an n-dodecane/n-tetradecane mixture.

According to at least one embodiment, the composition disclosed herein may comprise at least one volatile linear alkane in a total amount ranging from 0.5% to 95% by weight s, such as from 1% to 90% by weight, and further such as from 5% to 90% by weight, relative to the total weight of the composition.

The weight ratio of the at least one liquid volatile linear alkane to the at least one silicone copolymer based on silicone resin and fluid silicone has a value of greater than or equal to 2, such as from 2 to 100 and further such as from 2.5 to 50.

Pigments

The composition disclosed herein may further comprise at least one pigment.

By "pigment" is meant all of the pigments which provide color to keratin materials. Their solubility in water at 25° C. and at atmospheric pressure (760 mmHg) can be less than 0.05%, and such as less than 0.01%.

The at least one pigment can be chosen from organic pigments and mineral pigments that are known in the art, such as those described in Kirk-Othmer's Encyclopaedia of Chemical Technology and Ullmann's Encyclopaedia of Industrial Chemistry.

These pigments may be in the form of pigmentary powder or paste. These may be coated or uncoated.

The at least one pigment may be chosen, for example, from mineral pigments, organic pigments, lakes, special-effect pigments such as nacres, and metallic pigments and flakes.

The at least one pigment may be a mineral pigment. A mineral pigment can be any pigment which satisfies the definition in the Ullmann's encyclopaedia in the chapter on inorganic pigments. The mineral pigments, for example, include iron oxides or chromium oxides, manganese violet, ultramarine blue, chromium hydrate and Prussian blue, and titanium dioxide.

The at least one pigment may be a metallic particle comprising a pure metal or alloys of metals comprising more than 80% of metals by weight relative to the total weight of the metallic particle.

The at least one metallic particle can be present, for example, in the form of platelets. By "platelets" are meant particles in which the ratio of the largest dimension to the smallest dimension, referred to as shape factor, has a value of greater than or equal to 5.

By "dimensions" are meant the dimensions given by the statistical particle-size distribution for half of the population, referred to as D50. The at least one metallic particle may, for example, have a shape factor of greater than or equal to 8, and for example, greater than or equal to 8 to 10, and, for further example, greater than or equal to 15.

The at least one metallic particle may be chosen from silver, aluminium, iron, chromium, nickel, molybdenum, gold, copper, zinc, tin, magnesium, steel, bronze, titanium and alloys of these metals. The at least one metallic particle is, for example, chosen from copper, zinc, aluminium, titanium, silver, gold and alloys of these metals. For further example, the at least one metallic particle may be chosen from aluminium (for example having an aluminium content of greater than or equal to 99% by weight), copper (for example having a copper content of greater than or equal to 95% by weight), and bronze (for example having a copper content of from 70 to 95% and a zinc content of from 5% to 30%, by weight).

According to their greatest dimension, the at least one metallic particle may have, for example, an average size of less than or equal to 25 µm, for example, less than or equal to 10 µm.

By "average size" is meant the dimension given by the statistical particle-size distribution for half of the population, known as D50.

The at least one metallic particle may have a thickness of less than or equal to 1 µm, such as less than or equal to 0.7 µm, further such as less than or equal to 0.5 µm.

The at least one metallic particle disclosed herein may be chosen from, for example, particles of aluminium, such as those sold under the names STARBRITE 2100 EAC® by Silberline, and METALURE® by Eckart. Non-limiting mention may also be made of bronze powders such as those sold under the names PREMIOR SUPER 8000 by Wolstenholme and under the names ROTHOFLEX, LITHOFLEX and STANDARD by Eckart, with, for example, the references STANDARD BRONZE POWDER OFFSET 3000 SUPER PALE GOLD (D50 3-5 µm) and LITHOFLEX XA 40-03 RICH PALE GOLD (D50 3-5 µm). Non-limiting mention may also be made of particles of metal alloy, such as bronze powders coated with silica, which are sold under the name VISIONAIRE HONEY (size 5-50 µm) and under the name VISIONAIRE AMBER (size 5-50 µm) by Eckart, and also those sold under the name DOROLAN 08/0 PALE GOLD (D50 7-9 µm), the $SiO_2$-coated aluminium powder sold under the reference VISIONAIRE SILVER SEA (size 5-50 µm) and the $SiO_2$-coated copper powders sold under the reference VISIONAIRE CINNAMON (size 5-50 µm) and under the reference VISIONAIRE LAVA (size 5-50 µm) by Eckart, and also those sold under the name DOROLAN 10/0 COPPER (D50 9-11 µm).

The at least one pigment may be an organic pigment. By "organic pigment" is meant any pigment that may satisfy the definition in Ullmann's encyclopaedia in the chapter on organic pigments. The at least one organic pigment may, for example, be chosen from nitroso, nitro, azo, xanthene, quinoline, anthraquinone, phthalocyanine, isoindolinone, isoindoline, quinacridone, perinone, perylene, diketopyrrolopyrrole, thioindigo, dioxazine, triphenylmethane and quinophthalone compounds.

According to at least one embodiment, the at least one organic pigment may be chosen from carmine, carbon black, aniline black, azo yellow, quinacridone, phthalocyanine blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

The at least one organic pigment disclosed herein may also be in the form of composite pigments as described in patent EP 1 184 426. These composite pigments may be compounds of, for example, particles comprising an inorganic core, at least one binder for ensuring the binding of the organic pigments to the core, and at least one organic pigment at least partially covering the core.

The at least one organic pigment may also be a lake. By "lake" is meant dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate, and aluminium.

Among the dyes, non-limiting mention may be made of cochineal carmine. Non-limiting mention may also be made of the dyes known under the following names: D&C RED 21 (CI 45 380), D&C ORANGE 5 (CI 45 370), D&C RED 27 (CI 45 410), D&C ORANGE 10 (CI 45 425), D&C REDS (CI 45 430) D&C RED 4 (CI 15 510), D&C RED 33 (CI 17 200), D&C YELLOW 5 (CI 19 140), D&C YELLOW 6 (CI 15 985), D&C GREEN (CI 61 570), D&C YELLOW 10 (CI 77 002), D&C GREEN 3 (CI 42 053), D&C BLUE 1 (CI 42 090).

An example of a lake that may be mentioned is the product known under the following name: D&C RED 7 (CI 15 850:1).

The at least one pigment may also be a special effect pigment. By "special effect pigments" are meant pigments that generally create a non-uniform colored appearance (characterized by a certain shade, a certain vivacity and a certain lightness) that changes as a function of the conditions of observation (light, temperature, observation angles, etc.). They thus contrast with colored pigments that afford a standard uniform opaque, semi-transparent or transparent shade.

Non-limiting mention of special-effect pigments may be made of those with a low refractive index, such as fluorescent, photochromic or thermochromic pigments, and those with a higher refractive index, such as nacres or flakes.

Examples of special-effect pigments may include nacreous pigments such as mica coated with titanium dioxide, or with bismuth oxychloride, colored nacreous pigments such as mica coated with titanium dioxide and iron oxides, mica coated with iron oxide, mica coated with titanium dioxide and, for example, with Prussian blue or chromium oxide, mica coated with titanium dioxide and an organic pigment as defined above, and also nacreous pigments based on bismuth oxychloride. These pigments may also be mica particles superposed on their surface with at least two successive layers of metal oxides and/or organic colorants.

The nacres may, for example, possess a yellow, pink, red, bronze, orange, brown, gold and/or copper glint or color.

By way of illustration of the nacres that can be employed as disclosed herein, mention may be made of the gold-colored nacres sold, for example, by Engelhard under the name GOLD 222C (CLOISONNE), SPARKLE GOLD (TIMICA), GOLD 4504 (CHROMALITE) and MONARCH GOLD 233X (CLOISONNE); the bronze nacres sold, for example, by Merck under the name BRONZE FINE (17384) (COLORONA) and BRONZE (17353) (COLORONA), by Eckart under the name PRESTIGE BRONZE and PRESTIGE SOFT BRONZE, and by Engelhard under the name SUPER BRONZE (CLOISONNE); the orange nacres sold for example by Engelhard under the name ORANGE 363C (CLOISONNE) and ORANGE MCR 101 (COSMICA) and by Merck under the name PASSION ORANGE (COLORONA) and MATTE ORANGE (17449) (MICRONA); the brown-shade nacres sold, for example, by Engelhard under the name N-ANTIQUE COPPER 340XB (CLOISONNE) and BROWN CL4509 (CHROMALITE); the copper-glint nacres sold, for example, by Engelhard under the name COPPER 340A (TIMICA) and by Eckart under the name PRESTIGE COPPER and PRESTIGE SOFT COPPER; the red-glint nacres sold, for example, by Merck under the name SIENNA FINE (17386) (COLORONA); the yellow-glint nacres sold, for example, by Engelhard under the name YELLOW (4502) (CHROMALITE); the gold-glint red-shade nacres sold by Engelhard under the name SUNSTONE G012 (GEMTONE); the gold-glint black nacres sold, for example, by Englehard under the name NU ANTIQUE BRONZE 240 AB (TIMICA), the blue nacres sold, for example, by Merck under the name MATTE BLUE (17433) (MICRONA), DARK BLUE (117324) (COLORONA), the silver-glint white nacres sold, for example, by Merck under the name XIRONA SILVER, and the golden-green pink-orange nacres sold, for example, by Merck under the name INDIAN SUMMER (XIRONA) and mixtures thereof.

In addition to nacres on a mica support, it is also possible to envisage multi-layer pigments based on synthetic substrates such as alumina, silica, calcium sodium borosilicate or calcium aluminium borosilicate, and aluminium.

Non-limiting mention may also be made of pigments with an interference effect that are not fixed onto a substrate, for instance liquid crystals (HELICONES HC from Wacker), holographic interference flakes (GEOMETRIC PIGMENTS or SPECTRA F/X from Spectratek). Special-effect pigments may further comprise fluorescent pigments, whether these are substances that are fluorescent in daylight or that produce an ultraviolet fluorescence, phosphorescent pigments, photochromic pigments, thermochromic pigments and quantum dots, sold, for example, by Quantum Dots Corporation.

The variety of pigments that may be used in the present as disclosed herein makes it possible to obtain a rich palette of colors, and also certain optical effects such as metallic effects or interference effects.

The size of the at least one pigment disclosed herein may range from 10 nm to 200 µm, such as from 20 nm to 80 µm and further such as from 30 nm to 50 µm.

The at least one pigment may be dispersed in the composition via at least one dispersant.

The at least one dispersant is useful for protecting the dispersed particles against their agglomeration or flocculation. The at least one dispersant may be chosen from surfactants, oligomers, and polymers, bearing at least one functionality with strong affinity for the surface of the particles to be dispersed. For example, they can physically or chemically attach to the surface of the pigments. These dispersants may also contain at least one functional group that is compatible with or soluble in the continuous medium. For example, 12-hydroxystearic acid esters and C8 to C20 fatty acid esters of polyols such as glycerol or diglycerol can be used, such as poly(12-hydroxystearic acid) stearate with a molecular weight of about 750 g/mol, such as the product sold under the name SOLSPERSE 21 000 by the company Avecia, polyglyceryl-2 dipolyhydroxystearate (CTFA name) sold under the reference DEHYMYLS PGPH by the company Henkel, or poly-hydroxystearic acid such as the product sold under the reference ARLACEL P100 by the company Uniqema, and mixtures thereof.

As other dispersants that may be used in the compositions of the disclosure, mention may be made of quaternary ammonium derivatives of polycondensed fatty acids, for instance SOLSPERSE 17 000 sold by the company Avecia, and polydimethylsiloxane/oxypropylene mixtures such as those sold by the company Dow Corning under the references DC2-5185 and DC2-5225 C.

According to at least one embodiment, the at least one pigment may be surface-treated with at least one organic agent.

Thus, the at least one pigment that has been surface-treated beforehand, can be a pigment that has totally or partially undergone a surface treatment of chemical, electronic, electrochemical, mechanochemical or mechanical nature, with an organic agent such as those described, for example, in Cosmetics and Toiletries, February 1990, Vol. 105, pp. 53-64, before being dispersed in the composition disclosed herein. These organic agents may be chosen, for example, from amino acids; waxes, for example, carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example, aluminium stearate or laurate; metal alkoxides; polysaccharides, for example, chitosan, cellulose and derivatives thereof; polyethylene; (meth)acrylic polymers, for example, polymethyl methacrylates; polymers and copolymers containing acrylate units; proteins; alkanolamines; silicone compounds, for example, silicones, polydimethylsiloxanes, alkoxysilanes, alkylsilanes and siloxysilicates; organofluorine compounds, for example, perfluoroalkyl ethers; and fluorosilicone compounds.

The surface-treated pigments disclosed herein may also have been treated with a mixture of these compounds and/or may have undergone several surface treatments.

The surface-treated pigments disclosed herein may be prepared according to surface-treatment techniques that are well known to those skilled in the art, or may be commercially available in the required form.

According to at least one embodiment, the surface-treated pigments are coated with at least one organic layer.

The organic agent with which the pigments are treated may be deposited on the pigments by evaporation of solvent, chemical reaction between the molecules of the organic agent or creation of a covalent bond between the organic agent and the pigments.

The surface treatment may thus be performed, for example, by chemical reaction of a surface agent with the surface of the pigments and creation of a covalent bond between the surface agent and the pigments or the fillers. This method is, for example, described in U.S. Pat. No. 4,578,266.

For example, at least one organic agent covalently bonded to the pigments can be used.

The agent for the surface treatment may represent from 0.1% to 50% by weight, such as from 0.5% to 30% by weight and further such as from 1% to 10% by weight relative to the total weight of the surface-treated pigments.

When they are present, the amount of pigments can range from 0.1% to 40% by weight, such as from 0.5% to 20% by weight of the total weight of the composition.

Other Volatile Solvents

The composition disclosed herein may further comprise at least one additional volatile solvents in order to modify the rate of evaporation of the composition.

The at least one additional volatile solvent may be chosen from a non-silicone organic solvent and a silicone organic solvent other than the above-defined volatile linear alkanes.

Volatile non-silicone organic solvents that may be mentioned include:

volatile $C_1$-$C_4$ alkanols such as ethanol or isopropanol;

volatile non-linear $C_5$-$C_7$ alkanes such as 2,3-dimethylbutane, 2,2-dimethylbutane, 2-methyl-pentane or 3-methylpentane;

esters of liquid $C_1$-$C_{20}$ acids and of volatile $C_1$-$C_8$ alcohols such as methyl acetate, n-butyl acetate, ethyl acetate, propyl acetate, isopentyl acetate or ethyl 3-ethoxypropionate; isohexyl or isodecyl neopentanoate may also be mentioned;

ketones that are liquid at room temperature and volatile, such as methyl ethyl ketone, methyl isobutyl ketone, diisobutyl ketone, isophorone, cyclohexanone or acetone;

volatile polyols such as propylene glycol;

volatile ethers such as dimethoxymethane, diethoxyethane or diethyl ether;

volatile glycol ethers such as 2-butoxyethanol, butyl diglycol, diethylene glycol monomethyl ether, propylene glycol n-butyl ether or propylene glycol monomethyl ether acetate;

volatile non-linear hydrocarbon oils such as volatile branched hydrocarbon oils comprising from 8 to 16 carbon atoms, and mixtures thereof, and such as branched $C_8$-$C_{16}$ alkanes, for instance $C_8$-$C_{16}$ isoalkanes (also known as isoparaffins), isododecane, isodecane and, for example, the oils sold under the trade names ISOPAR or PERMETHYL, and mixtures thereof.

volatile $C_4$-$C_{10}$ perfluoroalkanes such as dodecafluoropentane, tetradecafluorohexane or decafluoropentane;

volatile perfluorocycloalkyls such as perfluoromethylcyclopentane, 1,3-perfluorodimeth-ylcyclohexane and perfluorodecalin, sold, respectively, for example, under the names FLUTEC PC1®, FLUTEC PC3® and FLUTEC PC6® by the company F2 Chemicals, and also perfluorodimethylcyclobutane and perfluoromorpholine;

the volatile fluoroalkyl or heterofluoroalkyl compounds corresponding to the following formula:

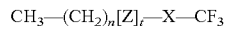

$$CH_3-(CH_2)_n[Z]_t-X-CF_3$$

in which t is 0 or 1; n is 0, 1, 2 or 3; X is a linear or branched divalent perfluoroalkyl radical comprising from 2 to 5 carbon atoms, and Z represents O, S or NR, R being a hydrogen atom or a radical $-(CH_2)_n-CH_3$ or a radical $-(CF_2)_m-CF_3$, m being 2, 3, 4 or 5.

Among the volatile fluoroalkyl or heterofluoroalkyl compounds that may be mentioned, for example, are methoxynonafluorobutane sold under the name MSX 4518® and HFE-7100® by the 3M Company, and ethoxynonafluorobutane sold under the name HFE-7200® by the 3M company.

For example, the solvent has a boiling point of less than 200° C.

According to at least one embodiment, the additional non-silicone organic solvent may be chosen from ethanol, isopropanol, acetone, and non-linear alkanes which are liquid at 25° C. and at atmospheric pressure (760 mmHg) such as isododecane.

Volatile silicone solvents that may be mentioned for illustration purpose include low-viscosity silicone compounds chosen from linear or cyclic silicones comprising from 2 to 7 silicon atoms, these silicones optionally comprising alkyl or alkoxy groups comprising from 1 to 10 carbon atoms, for example, octamethylcyclotetrasiloxane, decamethylcyclopentasiloxane, dodecamethylcyclohexasiloxane, heptamethyihexyltrisiloxane, heptamethylethyltrisiloxane, heptamethyloctyltrisiloxane, octamethyltrisiloxane and decamethyltetrasiloxane, and mixtures thereof. According to at least one embodiment, the silicone compound can be chosen from cyclopentadimethylsiloxane and dodecamethylcyclohexasiloxanes.

According to at least one embodiment, the volatile silicone solvent may have a viscosity of less than 50 centistokes.

For example, the volatile silicone can be chosen from decamethylcyclopentasiloxane, dodecamethylcyclohexasiloxane, octamethyltrisiloxane and decamethyltetrasiloxane.

Non-limiting examples that may be mentioned include the decamethylcyclopentasiloxane sold under the name DC-245 by the company Dow Corning, dodecamethylcyclohexasiloxane sold under the name DC-246 by the company Dow Corning, the octamethyltrisiloxane sold under the name DC-200 FLUID1 cSt by the company Dow Corning, and the decamethyltetrasiloxane sold under the name DC-200 FLUID 1.5 cSt by the company Dow Corning.

According to at least one embodiment, the at least one additional volatile solvent can be chosen from water, ethanol, isopropanol, acetone, isododecane, decamethylcyclopentasiloxane, dodecamethylcyclohexasiloxane, octamethyltrisiloxane, and decamethyltetrasiloxane.

The at least one additional volatile solvent may be present in the composition in a total amount ranging from 0.1% to 95% by weight, such as ranging from 1% to 90% by weight and further such as ranging from 5% to 90% by weight, relative to the total weight of the composition.

Additional Additives

According to at least one embodiment, the composition disclosed herein may further comprise at least one polysiloxane having a viscosity of greater than 100 cSt, such as greater than 300 cSt. The viscosity of the at least one polysiloxane can be measured according to ASTM standard D-445. The at least one polysiloxane may be chosen from silicone oils, gums or resins, and crosslinked silicones.

The at least one polysiloxane with a viscosity of greater than 100 cSt, for example, can include polydimethylsiloxanes; alkyl dimethicones; polyphenylmethylsiloxanes, such as phenyl dimethicones, phenyl trimethicones and vinylmethyl methicones; and also silicones modified with aliphatic and/or aromatic groups, which are optionally fluorinated, or with functional groups such as hydroxyl, thiol and/or amine groups.

The at least one polysiloxane may be chosen from the silicones of formula (I):

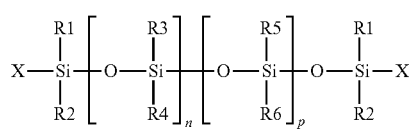

(I)

in which:
$R_1$, $R_2$, $R_5$ and $R_6$ are, together or separately, an alkyl radical comprising from 1 to 6 carbon atoms, $R_3$ and $R_4$ are, together or separately, an alkyl radical comprising from 1 to 6 carbon atoms, a vinyl radical, an aryl radical, an aminoalkyl radical comprising from 1 to 6 carbon atoms, which is optionally substituted, a hydroxyl radical or a thioalkyl radical comprising from 1 to 6 carbon atoms, and X is an alkyl radical comprising from 1 to 6 carbon atoms, a hydroxyl radical, a vinyl radical, an aminoalkyl radical comprising from 1 to 6 carbon atoms, which is optionally substituted, or a thioalkyl radical comprising from 1 to 6 carbon atoms, n and p being integers chosen so as to obtain a viscosity of greater than 300 cSt.

By way of example, mention may be made of the following polydimethylsiloxanes:

the substituents $R_1$ to $R_6$ and X represent a methyl group, such as the product sold under the name BAYSILICONE TP 3898 by the company General Electric, and the product sold under the name AK 500000 by the company Wacker, the substituents $R_1$ to $R_6$ and X represent a methyl group, p and n are such that the molecular weight is 120,000 g/mol, such as the product sold under the name Dow Corning 200 FLUID 60000 CS by the company Dow Corning, the substituents $R_1$ to $R_6$ and X represent a methyl group, p and n are such that the molecular weight is 250,000 g/mol, such as the product sold under the name MIRASIL DM 500.000 by the company Rhodia, and the product sold under the name Dow Corning 200 FLUID 500.000 cSt by the company Dow Corning, the substituents $R_1$ to $R_6$ represent a methyl group, the group X represents a hydroxyl group, n and p are such that the molecular weight of the polymer is 600,000 g/mol, such as the product sold under the name SGM 36 by the company Dow Corning, dimethicones of the (polydimethylsiloxane)(methylvinylsiloxane) type, such as SE63 sold by GE Bayer Silicones, poly(dimethylsiloxane)(diphenyl)(methylvinylsiloxane) copolymers, and mixtures thereof.

When the polysiloxane comprises a fluoro group, the copolymers having the following structure may be chosen:

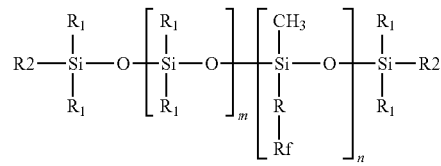

in which:
R represents a divalent, linear or branched alkyl group comprising 1 to 6 carbon atoms, such as a methyl, ethyl, propyl or butyl divalent group, Rf represents a fluoroalkyl radical, such as a perfluoroalkyl radical, comprising 1 to 12 carbon atoms, such as 1 to 9 carbon atoms, $R_1$ represents, independently of one another, a $C_1$-$C_{20}$ alkyl radical, a hydroxyl radical or a phenyl radical, $R_2$ represents $R_1$ or $R_f$, m is chosen from 0 to 500, such as from 0 to 200, and n is chosen from 1 to 1,000, such as from 1 to 500.

For example, the $R_1$ groups are identical and represent a methyl radical.

Such polysiloxanes are, for example, those sold by the company Shin Etsu under the names FL-5, FL-10, X22-821 and X22-822, or FL-100, by the company Dow Corning under the name FS-1265 FLUID, or by the company Phoenix Chemical under the PECOSIL FS range, under the names PECOSIL FSL-150, PECOSIL FSL-300, PECOSIL FSH-150, PECOSIL FSH-300, PECOSIL FSU-150 and PECOSIL FSU-300.

The weight-average molecular mass of the polysiloxane(s) may range from 1000 to 1,500,000 g/mol, such as from 20,000 to 1,000,000 g/mol.

The at least one polysiloxane may take the form of a resin. By "resin" is meant a crosslinked or noncrosslinked three-dimensional structure. By way of example of a polysiloxane resin, mention may be made of silsesquioxanes and siloxysilicates.

The nomenclature of silicone resins can be known as "MDTQ", the resin being described as a function of the various siloxane monomeric units that it comprises, each of the letters "MDTQ" characterizing one type of unit.

The letter M represents the monofunctional unit of formula $(CH_3)_3SiO_{1/2}$, the silicon atom being linked to a single oxygen atom in the polymer comprising this unit.

The letter D signifies a difunctional $(CH_3)_2SiO_{2/2}$ unit in which the silicon atom is linked to two oxygen atoms.

The letter T represents a trifunctional unit of formula $(CH_3)SiO_{3/2}$.

In the M, D and T units defined above, at least one of the methyl groups can be substituted with a group R different from the methyl group, such as a hydrocarbon-based (for example alkyl) radical comprising from 2 to 10 carbon atoms, or a phenyl group, or alternatively a hydroxyl group.

Finally, the letter Q signifies a tetrafunctional $SiO_{4/2}$ unit in which the silicon atom is linked to four hydrogen atoms, themselves linked to the rest of the polymer.

Various resins having different properties can be obtained from these various units, the properties of these polymers varying according to the type of monomers (or units), to the type and number of radicals substituted, to the length of the polymer chain, to the degree of branching and/or to the size of the pendent chains.

By way of example of these silicone resins, mention may be made of:

siloxysilicates which can be trimethylsiloxysilicates of formula $[(CH_3)_3SiO]_x(SiO_{4/2})_y$ (MQ units) in which x and y are integers ranging from 50 to 80, polysilsesquioxanes of formula $(CH_3SiO_{3/2})_x$ (T units) in which at least one of the methyl radicals can be substituted with a group R as defined above. For example, the number x of T units of the silsesquioxane is less than or equal to 500, it can be from 50 to 500. The molecular weight of the silicone resin disclosed herein can therefore be from 500 to 50,000 g/mol, such as from 500 to 20,000 g/mol, and further such as from 500 to 10,000 g/mol;

polymethylsilsesquioxanes which are polysilsesquioxanes in which none of the methyl radicals are substituted with another group. Such polymethylsilsesquioxanes are, for example, described in U.S. Pat. No. 5,246,694;

polypropylsilsesquioxanes, in which the methyl radicals are replaced with propyl radicals. These compounds, and also the synthesis thereof, are, for example, described in International Application Publication No. WO 2005/075567;

polyphenylsilsesquioxanes, in which the methyl radicals are replaced with phenyl radicals. These compounds, and also the synthesis thereof, are, for example, described in US 2004/0180011.

By way of examples of commercially available polymethylsilsesquioxane resins, mention may be made of those which are marketed:

by the company Wacker under the reference RESIN MK, such as BELSIL PMS MK: polymer comprising repeating $CH_3SiO_{3/2}$ units (T units) that may also comprise up to 1% by weight of $(CH_3)_2SiO_{2/2}$ units (D units) and that has an average molecular weight of 10,000 g/mol. It is thought that the polymer may be in a "cage" and "ladder" configuration as is represented in the figures below. The average molecular weight of the units in the "cage" configuration was calculated at 536 g/mol. The majority of the polymer is in the "ladder" configuration with ethoxy groups at the ends. These ethoxy groups represent 4.5% by mass of the polymer. Since these ends can react with water, a small and variable amount of SiOH groups may also be present.

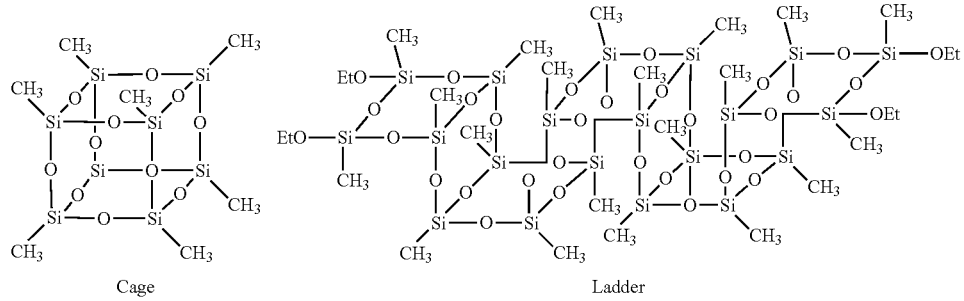

Cage                                          Ladder by the company Shin-Etsu under the references KR-220L, which comprise T units of formula $CH_3SiO_{3/2}$ and have SiOH (silanol) terminal groups, under the reference KR-242A, which comprise 98% of T units and 2% of dimethyl units D and have SiOH terminal groups, or else under the reference KR-251, comprising 88% of T units and 12% of dimethyl units D and having SiOH terminal groups.

By way of examples of commercially available polypropylsilsesquioxane resins, mention may be made of those which are marketed:

by the company Dow Corning under the reference Dow Corning 670 FLUID, which is a polypropylsilsesquioxane diluted in D5.

By way of examples of commercially available polyphenylsilsesquioxane resins, mention may be made of those which are marketed:

by the company Dow Corning under the reference Dow Corning 217 FLAKE Resin, which is a silanol-terminated polyphenylsilsesquioxane;

by the company Wacker under the reference BELSIL SPR 45 VP.

As siloxysilicate resins, non-limiting mention may be made of trimethylsiloxysilicate (TMS) resins, optionally in the form of powders. Such resins are, for example, marketed under the reference SR1000 by the company General Electric or under the reference TMS 803 by the company Wacker. Mention may also be made of the trimethylsiloxysilicate resins marketed in a solvent such as cyclomethicone, sold under the name KF-7312J by the company Shin-Etsu, and DC 749 and DC 593 by the company Dow Corning.

According to at least one embodiment, the at least one silicone resin is film-forming. In fact, not all silsesquioxanes are film-forming, for example, the highly polymerized polymethylsilsesquioxanes such as TOSPEARL™ from Toshiba or KMP590 from Shin-Etsu are insoluble and are not film-forming.

According to at least one embodiment, the at least one silicone resin is soluble or dispersible in the composition. For example, the at least one silicone resin disclosed herein can be soluble in volatile silicones and organic solvents. According to at least one embodiment, the at least one silicone resin is solid at 25° C.

According to at least one embodiment, the at least one silicone resin can be chosen from trimethylsiloxysilicate resins, polymethylsilsesquioxane resins and polypropylsilsesquioxane resins.

The composition disclosed herein may also comprise at least one crosslinked silicone such as a crosslinked elastomeric organopolysiloxane, which is a high-molecular-weight silicone compound having a three-dimensional structure, with the viscoelastic properties of a flexible solid material. The at least one organopolysiloxane may thus be in powdered dry form, or in swollen form, or in a solvent, the resulting product, for example, being a gel. These products may also be in a form dispersed in an aqueous solvent.

The synthesis of these organopolysiloxanes is described, for example, in the following publications:

U.S. Pat. No. 5,266,321 from Kobayashi Kose,
U.S. Pat. No. 4,742,142 from Toray Silicone,
U.S. Pat. No. 5,654,362 from Dow Corning Corp.,
patent application FR 2 864 784.

The at least one elastomeric organopolysiloxane used in the composition may be partially or totally crosslinked. They can be in the form of particles. For example, the elastomeric organopolysiloxane particles may have a number-average size ranging from 0.1 to 500 µm. These particles may be of any shape, and, for example, may be spherical, flat or amorphous.

The at least one crosslinked organopolysiloxane may be a non-emulsifying compound or an emulsifying compound. The term "non-emulsifying" defines crosslinked organopolysiloxanes which do not contain polyoxyalkylene units. The term "emulsifying" signifies crosslinked organopolysiloxane compounds having at least one polyoxyalkylene, for example, polyoxyethylene or polyoxypropylene, unit.

The crosslinked organopolysiloxane particles may be conveyed in the form of a gel comprising at least one crosslinked organopolysiloxane included in at least one hydrocarbon-based oil and/or one silicone oil. In these gels, the organopolysiloxane particles are, for example, non-spherical particles. The crosslinked organopolysiloxane particles may also be in the form of a powder, for example, in the form of a spherical powder.

Non-emulsifying crosslinked organopolysiloxanes are, for example, described in U.S. Pat. No. 4,970,252, U.S. Pat. No. 4,987,169, U.S. Pat. No. 5,412,004, U.S. Pat. No. 5,654,362 and U.S. Pat. No. 5,760,116, and in application JP-A-61-194009.

As non-emulsifying crosslinked organopolysiloxanes, non-limiting mention may be made of those sold under the names KSG-6, KSG-15, KSG-16, KSG-18, KSG-31, KSG-32, KSG-33, KSG-41, KSG-42, KSG-43, KSG-44 and USG-103 by the company Shin-Etsu, DC 9040, DC 9041, DC 9509, DC 9505, DC 9506 and DC 9045 by the company Dow Corning, GRANSIL by the company Grant Industries, and SFE 839 by the company General Electric.

For example, the emulsifying crosslinked organopolysiloxanes comprise polyoxyalkylene-modified organopolysiloxanes formed from divinyl compounds, such as polysiloxanes having at least two vinyl groups, which react with Si—H bonds of a polysiloxane. Emulsifying crosslinked organopolysiloxanes are, for example, described in U.S. Pat. No. 5,236,986, U.S. Pat. No. 5,412,004, U.S. Pat. No. 5,837,793 and U.S. Pat. No. 5,811,487.

As emulsifying crosslinked organopolysiloxanes, non-limiting mention may be made of those marketed under the names KSG-21, KSG-20 and KSG-30 by the company Shin Etsu, and DC 9010 and DC 9011 by the company Dow Corning.

The particles of elastomeric crosslinked organopolysiloxane may also be in the form of a powder of elastomeric crosslinked organopolysiloxane coated with at least one silicone resin, for example, with silsesquioxane resin, as described, for example, in U.S. Pat. No. 5,538,793.

Such elastomers are, for example, sold under the names KSP-100, KSP-101, KSP-102, KSP-103, KSP-104 and KSP-105 by the company Shin Etsu.

According to at least one embodiment, the at least one crosslinked organopolysiloxane is non-emulsifying.

The composition disclosed herein may also comprise at least one grafted silicone polymer. As indicated herein, the term "grafted silicone polymer" is intended to mean a polymer comprising a polysiloxane portion and a portion constituted of a non-silicone organic chain, one of the two portions constituting the main chain of the polymer, the other being grafted onto said main chain.

The at least one grafted silicone polymer is, for example, chosen from polymers having a non-silicone organic backbone grafted with monomers comprising a polysiloxane and polymers having a polysiloxane backbone grafted with non-silicone organic monomers.

The non-silicone organic monomers constituting the main chain of the at least one grafted silicone polymer may be chosen from free-radically polymerizable, ethylenically unsaturated monomers, polycondensation-polymerizable monomers, such as those forming polyamides, polyesters or polyurethanes, and ring-opening monomers such as those of the oxazoline or caprolactone type.

The polymers having a non-silicone organic backbone grafted with monomers containing a polysiloxane, can be, for example, chosen from those described in U.S. Pat. No. 4,693,935, U.S. Pat. No. 4,728,571 and U.S. Pat. No. 4,972,037 and patent applications EP-A-0 412 704, EP-A-0 412 707, EP-A-0 640 105 and International Application Publication No. WO 95/00578. They can be copolymers obtained by free-radical polymerization starting from ethylenically unsaturated monomers and silicone macromers having a terminal vinyl group, or else copolymers obtained by reaction of a polyolefin comprising functionalized groups and of a polysiloxane macromer having a terminal function that is reactive with said functionalized groups.

The at least one copolymer having a non-silicone organic backbone grafted with monomers comprising a polysiloxane may, for example, have the following structure:

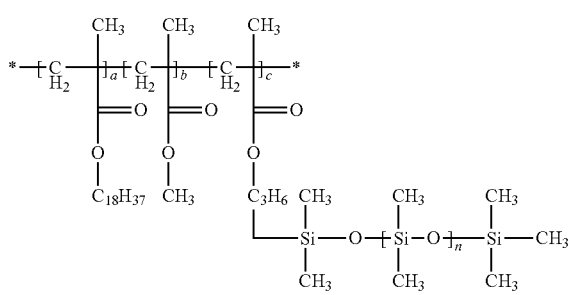

Such a polymer is, for example, marketed under the name KP 561 by Shin Etsu.

The at least one copolymer having a non-silicone organic backbone grafted with monomers comprising a polysiloxane may also have the following structure:

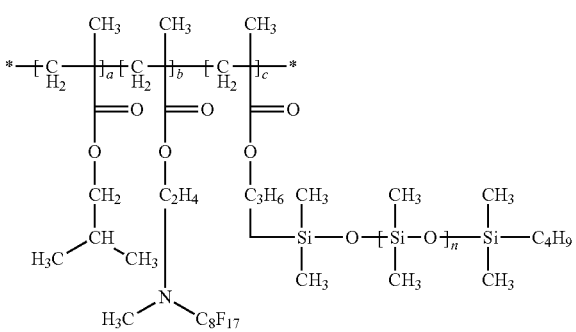

Such a polymer, POLYSILICONE 7, is, for example, marketed under the name SA70 by 3M.

Other copolymers having a non-silicone organic backbone grafted with monomers comprising a polysiloxane may also be KP545, KP574 and/or KP575, marketed by Shin Etsu.

As a grafted silicone compound, mention may also be made of the isobutyl methacrylate/bis(hydroxypropyl) dimethicone acrylate copolymer sold by Grant Industries under the name GRANACRYSIL BMAS.

According to at least one embodiment, the at least one grafted silicone polymer, having a polysiloxane backbone grafted with non-silicone organic monomers, comprises a main chain of silicone (or polysiloxane ($\equiv$Si—O—)$_n$) onto which is grafted, within said chain and also, optionally, at at least one of its ends, at least one organic group which does not comprise silicone.

Non-limiting examples of the at least one grafted silicone polymer corresponding to the above definition include polydimethylsiloxanes (PDMSs) onto which are grafted, via a thiopropylene-type connecting chain, mixed polymer units of the poly(meth)acrylic acid type and of the poly(alkyl (meth) acrylate) type. As a compound corresponding to this definition, non-limiting mention may be made of polydimethylsiloxane or polymethylsiloxane comprising methyl 3-(propylthio)acrylate/methyl methacrylate/-methacrylic acid groups, or POLYSILICONE-8 marketed under the name VS80 by the company 3M.

Other examples of the at least one grafted silicone polymer include polydimethylsiloxanes (PDMSs) onto which are grafted, via a thiopropylene-type connecting chain, polymer units of the poly(isobutyl (meth)acrylate) type.

According to at least one embodiment, the number-average molecular mass of the at least one silicone polymer having a polysiloxane backbone grafted with non-silicone organic monomers, ranges from 10,000 to 1,000,000, and for example from 10,000 to 100,000.

According to at least one embodiment, the at least one grafted silicone polymer can be chosen from polydimethylsiloxane-grafted alkyl methacrylate copolymer, isobutyl methacrylate/acrylic acid/silicone macromer copolymers and polydimethylsiloxane or polymethylsiloxane comprising methyl 3-(propylthio)acrylate/methyl methacrylate/methacrylic acid groups.

For example, the at least one additional silicone compound can be chosen from silicone oils, such as those described in formula (I), and silicone resins.

When they are present in the composition disclosed herein, the total amount of the at least one additional silicone compound ranges from 0.1% to 30% by weight, such as from 0.1% to 20% by weight, and further such as from 0.1% to 10% by weight of the total weight of the composition.

The composition disclosed herein may further comprise at least one thickener chosen from polymeric thickeners and inorganic thickeners.

The at least one thickener may be inorganic or organic, and polymeric or non-polymeric. The at least one thickener may be chosen to thicken an aqueous phase or a fatty phase of the composition, as appropriate.

The term "thickener" is intended to mean a compound that modifies the rheology of the medium into which it is incorporated by increasing by at least 100 cps the viscosity of the medium at 25° C. and at a shear rate of 1 s$^{-1}$. This viscosity can be measured using a cone/plate viscometer (Haake R600 Rheometer, or similar).

The at least one aqueous-medium thickener may be chosen from:

hydrophilic clays, hydrophilic fumed silica, water-soluble cellulose-based thickeners, such as hydroxyethylcellulose, methylcellulose or hydroxypropylcellulose. Among these, non-limiting mention may be made of the gums sold under the name CELLOSIZE QP 4400 H by the company Amerchol, nonionic guar gums comprising $C_1$-$C_6$ hydroxyalkyl groups. By way of example, mention may be made of hydroxymethyl, hydroxypropyl and hydroxybutyl groups. Such guar gums are, for example, sold under the trade names JAGUAR HP8, JAGUAR HP60, JAGUAR HP120 and JAGUAR HP105 by the company Meyhall or under the name GALACTASOL 40H4FD2 by the company Aqualon, carrageenans, locust bean gum, scleroglucan gum, gellan gum, rhamsan gum and karaya gum, alginates, maltodextrins, starch and derivatives thereof, and hyaluronic acid and salts thereof, polyglyceryl(meth)acrylate polymers sold under the names HISPAGEL or LUBRAGEL by the companies Hispano Quimica or Guardian, polyvinyl alcohol, crosslinked acrylamide polymers and copolymers, such as those sold under the names PAS 5161 or BOZEPOL C by the company Hoechst, SEPIGEL 305 by the company Seppic by the company Allied Colloid, or the crosslinked methacryloyloxyethyltrimethylammonium chloride homopolymers sold under the name SALCARE SC95 by the company Allied Colloid, and associative polymers, and, for example, associative polyurethanes.

Such thickeners are, for example, described in application EP-A-1400234, the content of which is incorporated herein by reference.

The at least one oily-medium thickener may be chosen from:
organophilic clays;
hydrophobic fumed silicas;
alkyl guar gums (with a $C_1$-$C_6$ alkyl group), such as those described in EP-A-708114;
oil-gelling polymers, for instance triblock polymers or star polymers resulting from the polymerization or copolymerization of at least one monomer comprising an ethylenic group, for instance the polymers sold under the name KRATON;
polymers with a weight-average molecular mass of less than 100,000, comprising a) a polymer backbone comprising hydrocarbon-based repeating units comprising at least one heteroatom, and optionally b) at least one pendent fatty chain and/or at least one terminal fatty chain, which are optionally functionalized, comprising from 6 to 120 carbon atoms and being linked to these hydrocarbon-based units, as described in International Application Publication Nos. WO02/056847 and WO02/47619, the content of which is incorporated herein by reference; such as, polyamide resins (for example, comprising alkyl groups comprising from 12 to 22 carbon atoms) such as those described in U.S. Pat. No. 5,783,657;
the silicone-based polyimide resins as described in patent application EP-A-1266647 and in the French patent application FR 0 216 039.

Such thickeners are, for example, described in application EP-A-1400234, the content of which is incorporated herein by reference.

The at least one thickener may be an organic gelling agent, i.e. an agent comprising at least one organic compound. The at least one organogelling agent may be chosen from those described in International Application Publication No. WO03/105788.

According to at least one embodiment, the at least one polymeric thickener is an amorphous polymer formed by polymerization of an olefin. The olefin may, for example, be an elastomeric ethylenically unsaturated monomer.

As examples of olefins, non-limiting mention may be made of ethylenic carbide monomers, for example, comprising one or two ethylenic unsaturations, and comprising from 2 to 5 carbon atoms, such as ethylene, propylene, butadiene or isoprene.

The at least one polymeric thickener is capable of thickening or gelling the composition. By "amorphous polymer" is meant a polymer that does not have a crystalline form. The at least one polymeric thickener may also be film-forming.

The at least one polymeric thickener may, for example, be a diblock, triblock, multiblock, radial or star copolymer, or mixtures thereof.

Such polymeric thickeners are, for example, described in US2002/005562 and in U.S. Pat. No. 5,221,534.

According to at least one embodiment, the at least one polymeric thickener is an amorphous block copolymer of styrene and of olefin.

The at least one polymeric thickener is, for example, hydrogenated to reduce the residual ethylenic unsaturations after the polymerization of the monomers.

According to at least one embodiment, the at least one polymeric thickener is an optionally hydrogenated copolymer, comprising styrene blocks and ethylene/C3-C4 alkylene blocks.

As diblock copolymers, that are, for example, hydrogenated, non-limiting mention may be made of styrene-ethylene/propylene copolymers and styrene-ethylene/butadiene copolymers. Diblock polymers are, for example, sold under the name KRATON® G1701E by the company Kraton Polymers.

As triblock copolymers, that are, for example, hydrogenated, non-limiting mention may be made of styrene-ethylene/propylene-styrene copolymers, styrene-ethylene/butadiene-styrene copolymers, styrene-isoprene-styrene copolymers and styrene-butadiene-styrene copolymers. Triblock polymers are, for example, sold under the names KRATON® G1650, KRATON® G1652, KRATON® D1101, KRATON® D1102 and KRATON® D1160 by the company Kraton Polymers.

Further non-limiting mention may also be made of a mixture of styrene-butylene/ethylene-styrene triblock hydrogenated copolymer and of ethylene-propylene-styrene hydrogenated star polymer, such a mixture being, for example, in isododecane. Such mixtures are, for example, sold by the company Penreco under the trade names VERSAGEL® M5960 and VERSAGEL® M5670.

According to at least one embodiment, a diblock copolymer such as those described previously, for example, a styrene-ethylene/propylene diblock copolymer, can be used as the at least one polymeric thickener.

According to at least one embodiment, the organic clays are clays modified with chemical compounds that make the clay capable of swelling.

Clays can be products already known per se, which are described, for example, in the book "Mineralogie des argiles" [Clay Mineralogy], S. Caillère, S. Hénin, M. Rautureau, $2^{nd}$ edition 1982, Masson, the teaching of which is incoporated herein by reference.

Clays can be silicates comprising at least one cation that may be chosen from calcium, magnesium, aluminium, sodium, potassium and lithium cations.

By way of examples of such products, mention may be made of clays of the smectite family, such as montmorillonites, hectorites, bentonites, beidellites and saponites, and also of the family of vermiculites, stevensite and chlorites.

These clays may be of natural or synthetic origin. For example, clays that are cosmetically compatible and acceptable with keratin materials are used.

The at least one organophilic clay may be chosen from montmorillonite, bentonite, hectorite, attapulgite and sepiolite. The at least one organophilic clay is, for example, a bentonite or a hectorite.

These clays may be modified with at least one chemical compound chosen from quaternary amines, tertiary amines, amine acetates, imidazolines, amine soaps, fatty sulphates, alkyl aryl sulphonates and amine oxides.

As organophilic clays, non-limiting mention may be made of quaternium-18 bentonites such as those sold under the names BENTONE 3, BENTONE 38 and BENTONE 38V by the company Rheox, TIXOGEL VP by the company United Catalyst, CLAYTONE 34, CLAYTONE 40 and CLAYTONE XL by the company Southern Clay; stearalkonium bentonites such as those sold under the names BENTONE 27 by the company Rheox, TIXOGEL LG by the company United Catalyst and CLAYTONE AF and CLAYTONE APA by the company Southern Clay; quaternium-18/benzalkonium bentonites such as those sold under the names CLAYTONE HT and CLAYTONE PS by the company Southern Clay.

The fumed silicas may be obtained by high-temperature hydrolysis of a volatile silicon compound in an oxyhydrogen flame, producing a finely divided silica. This process makes it possible, for example, to obtain hydrophilic silicas having a large number of silanol groups at their surface. Such hydrophilic silicas are, for example, marketed under the names AEROSIL 130®, AEROSIL 200®, AEROSIL 255®, AEROSIL 300® and AEROSIL 380® by the company Degussa, and CAB-O-SIL HS-5®, CAB-O-SL EH-5®, CAB-O-SIL LM-130®, CAB-O-SIL MS-55® and CAB-O-SIL M-5® by the company Cabot.

It is possible to modify chemically the surface of said silica, via a chemical reaction generating a reduction in the number of silanol groups. It is, for example, possible to substitute silanol groups with hydrophobic groups; a hydrophobic silica can be then obtained.

The hydrophobic groups may be:

trimethylsiloxyl groups, which are obtained, for example, by treating fumed silica in the presence of hexamethyldisilazane. Silicas thus treated are known as "silica silylate" according to the CTFA ($6^{th}$ edition, 1995). They are, for example, marketed under the references AEROSIL R812® by the company Degussa and CAB-O-SIL TS-530® by the company Cabot;

dimethylsilyloxyl or polydimethylsiloxane groups, which are, for example, obtained by treating fumed silica in the presence of polydimethylsiloxane or of dimethyl-dichlorosilane. Silicas thus treated are known as "silica dimethyl silylate" according to the CTFA ($6^{th}$ edition, 1995). They are, for example, marketed under the references AEROSIL R972® and AEROSIL R974® by the company Degussa, and CAB-O-SIL TS-610® and CAB-O-SIL TS-720® by the company Cabot.

The fumed silica, for example, has a particle size that may be nanometric to micrometric, for example, ranging from 5 to 200 nm.

According to at least one embodiment, an organomodified bentonite or hectorite can beused as inorganic thickener.

The at least one thickener may be present in the composition in a total amount ranging from 0.1% to 10% by weight, relative to the total weight of the composition, such as ranging from 0.5% to 7% by weight, and further such as ranging from 0.5% to 4% by weight.

The compositions disclosed herein may also comprise at least one agent that can be used in cosmetics, chosen, for example, from reducing agents, fatty substances, plasticizers, softeners, antifoams, moisturizers, UV-screening agents, inorganic colloids, peptizers, solubilizers, fragrances, proteins, vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

The above additives can be present in an amount for each of them ranging from 0.01% to 20% by weight, relative to the weight of the composition.

Of course, those skilled in the art will take care to choose this or these optional additive(s) in such a way that the beneficial properties intrinsically associated with the formation of the coating are not, or are not substantially, impaired.

The composition disclosed herein may, for example, be in the form of a suspension, a dispersion, a solution, a gel, an emulsion, such as an oil-in-water (O/W) or water-in-oil (W/O) emulsion or a multiple emulsion (W/O/W or polyol/O/W or O/W/O), in the form of a cream, a mousse, a stick, a dispersion of vesicles, such as of ionic or nonionic lipids, a two-phase or multi-phase lotion, a spray, a powder or a paste.

The composition may be an anhydrous composition, i.e. a composition comprising less than 2% by weight of water, or even less than 0.5% of water, for example, free of water, the water not being added during the preparation of the composition, but corresponding to the residual water introduced by the mixed ingredients. The composition may also be in lacquer form.

The composition described above may be used on dry or wet hair. The additives described above, when present, may be applied to the hair simultaneously with the composition of the present disclosure or separately. The composition may be rinsed off or not. It is also possible to carry out washing of the hair subsequently, though such washing is not mandatory.

It is also possible to use a method of application with heating. According to at least one embodiment, application to the hair may be performed, for example, using a comb, a fine brush, a coarse brush or the fingers.

Application of the composition can be subsequently followed by drying at a temperature above 40° C. According to at least one embodiment this temperature is above 45° C. According at least one embodiment this temperature is above 45° C. and below 220° C.

The drying can be carried out immediately after the application or after a leave-in time that can range from 1 minute to 30 minutes.

According to at least one embodiment, in addition to a supply of heat, the hair can be dried using a flow of air. This flow of air during drying makes it possible to improve the individualization of the coating.

During drying, a mechanical action on the locks may be exerted, such as combing, brushing or running the fingers through.

The drying step of the method disclosed herein may be performed with a hood, a hairdryer, and/or a straightener, etc.

When the drying step is performed with a hood or a hairdryer, the drying temperature can range from 40 to 110° C., such as from 50 to 90° C.

When the drying step is performed with a straightener, the drying temperature can range from 110° C. to 220° C., such as from 140° C. to 200° C. degrees.

Once the drying is complete, a final rinse or shampoo wash may optionally be performed.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. By way of non-limiting illustration, concrete examples of certain embodiments of the present disclosure are given below.

The present disclosure can be more fully illustrated with the aid of the following, non-limiting examples.

EXAMPLES

Example 1

The following compositions were prepared:

| Composition | A (according to the disclosure) | A' (comparative) |
|---|---|---|
| BIOPSA DC 7-4405, 40% in isododecane, sold by Dow Corning | 17.5 g | 17.5 g |
| alpha, omega-dihydroxy PDMS gum of very high molecular weight | 1.5 g | 1.5 g |
| n-Undecane/n-tridecane mixture, the amount of n-undecane being predominant in the mixture* | qs 100 g | — |
| Isododecane | — | qs 100 g |

*as prepared in accordance with patent application WO 2008/155059

0.3 g of composition A was applied to a 1 g lock of clean, dry hair with a tone level of 4. After a waiting time of 2 minutes, the lock was blown-dry with a hairdryer at a temperature of 80° C. for 2 minutes. This gave a lock in which the individual hairs were separate and had body, the volumization obtained being durable to shampooing.

When 0.3 g of composition A' was applied under the same conditions to a 1 g lock of clean, dry hair with a tone level of 4, blow-drying of the lock with a hairdryer was more difficult to perform, with the brush running less easily through the hair.

Example 2

The following composition was prepared:

| Composition | |
|---|---|
| BIOPSA DC 7-4405, 40% in isododecane, sold by Dow Corning | 17.5 g |
| alpha, omega-dihydroxy PDMS gum of very high molecular weight | 1.5 g |
| Polymethylsilsesquioxane sold under the name BELSIL PMS MK Powder by the company Wacker | 3 g |
| Disteardimonium hectorite (10%) and propylene carbonate (3%) in isododecane, sold by Elementis under the name BENTONE GEL ISD V | 15 g |
| n-Undecane/n-tridecane mixture, the amount of n-undecane being predominant in the mixture* | 30 g |
| Isododecane | qs 100 g |

*as prepared in accordance with patent application WO 2008/155059

0.3 g of the composition was applied to a 1 g lock of clean, dry hair with a tone level of 4. After a waiting time of 2 minutes, the lock was blown-dry with a hairdryer at a temperature of 80° C. for 2 minutes. This gave a lock in which the individual hairs were separate and had body, the volumization obtained being durable to shampooing.

Example 3

The following compositions were prepared:

| Composition | B(according to the disclosure) | B' (comparative) |
|---|---|---|
| BIOPSA DC 7-4405, 40% in isododecane, sold by Dow Corning | 17.5 g | 17.5 g |
| alpha, omega-dihydroxy PDMS gum of very high molecular weight | 1.5 g | 1.5 g |
| Brown iron oxide-coated mica nacre, sold by Eckart under the name PRESTIGE SOFT BRONZE | 5 g | 5 g |
| n-Undecane/n-tridecane mixture, the amount of n-undecane being predominant in the mixture* | qs 100 g | — |
| Isododecane | — | qs 100 g |

*as prepared in accordance with patent application WO 2008/155059

0.6 g of composition B was applied to a 1 g lock of clean, dry hair with a tone level of 4. After a waiting time of 2 minutes, the lock was blown-dry with a hairdryer at a temperature of 80° C. for 2 minutes. This gave a colored lock in which the individual hairs were separate and the color was very uniform and durable to shampooing.

When 0.6 g of composition B' was applied under the same conditions to a 1 g lock of clean, dry hair with a tone level of 4, blow-drying of the lock with a hairdryer was more difficult to perform, with the brush running less easily through the hair.

Example 4

The following composition was prepared:

| Composition | |
|---|---|
| BIOPSA DC 7-4405, 40% in isododecane, sold by Dow Corning | 17.5 g |
| alpha, omega-dihydroxy PDMS gum of high molecular weight | 1.5 g |
| Brown iron oxide-coated mica nacre, sold by Eckart under the name PRESTIGE SOFT BRONZE | 5 g |
| Polymethylsilsesquioxane sold under the name BELSIL PMS MK Powder by the company Wacker | 3 g |
| Disteardimonium hectorite (10%) and propylene carbonate (3%) in isododecane, sold by Elementis under the name BENTONE GEL ISD V | 15 g |
| n-Undecane/n-tridecane mixture, the amount of n-undecane being predominant in the mixture* | 20 g |
| Isododecane | qs 100 g |

*as prepared in accordance with patent application WO 2008/155059

0.6 g of the composition was applied to a 1 g lock of clean, dry hair with a tone level of 4. After a waiting time of 2 minutes, the lock was blown-dry with a hairdryer at a temperature of 80° C. for 2 minutes. This gave a colored lock in which the individual hairs were separate and the color was very uniform and durable to shampooing.

Example 5

The following composition was prepared:

| Composition | |
|---|---|
| BIOPSA DC 7-4405, 40% in isododecane, sold by Dow Corning | 17.5 g |
| alpha, omega-dihydroxy PDMS gum of high molecular weight | 1.5 g |
| Brown iron oxide-coated mica nacre, sold by Eckart under the name PRESTIGE SOFT BRONZE | 5 g |
| Polymethylsilsesquioxane sold under the name BELSIL PMS MK Powder by the company Wacker | 3 g |
| Disteardimonium hectorite (10%) and propylene carbonate (3%) in isododecane, sold by Elementis under the name BENTONE GEL ISD V | 15 g |
| n-Undecane/n-tridecane mixture, the amount of n-undecane being predominant in the mixture* | qs 100 g |

*as prepared in accordance with patent application WO 2008/155059

0.6 g of the composition was applied to a 1 g lock of clean, dry hair with a tone level of 4. After a waiting time of 2 minutes, the lock was blown-dry with a hairdryer at a temperature of 80° C. for 2 minutes. This gave a colored lock in which the individual hairs were separate and the color was very uniform and durable to shampooing.

What is claimed is:

1. A cosmetic composition for treating keratin fibers, comprising at least one silicone copolymer based on at least one silicone resin and at least one fluid silicone, and at least one liquid volatile linear alkane mixture chosen from a mixture of n-undecane/n-tridecane (C11/C13),
    wherein the weight ratio of the at least one liquid volatile linear alkane mixture to the at least one silicone copolymer has a value greater than or equal to 2; and
    wherein the C11 volatile linear alkane, n-undecane, is present in an amount ranging from about 55% to about 80% by weight, and the C13 volatile linear alkane, n-tridecane, is present in an amount ranging from about 20% to about 45% by weight, relative to the total weight of the n-undecane/n-tridecane (C11/C13) mixture.

2. The cosmetic composition according to claim 1, wherein the at least one silicone resin is present in a total amount ranging from 45% to 75% by weight of the total weight of the at least one silicone copolymer, and the at least one fluid silicone is present in a total amount ranging from 25% to 55% by weight of the total weight of the at least one copolymer, with the sum of the percentages of silicone resin and fluid silicone being equal to 100.

3. The cosmetic composition according to claim 2, wherein the at least one silicone resin is present in a total amount ranging from 55% to 65% by weight of the total weight of the at least one silicone copolymer, and the at least one fluid silicone is present in a total amount ranging from 35% and 45% by weight of the total weight of the at least one copolymer, with the sum of the percentages of the at least one silicone resin and the at least one fluid silicone being equal to 100.

4. The cosmetic composition according to claim 1, wherein the at least one silicone copolymer is present in a total amount of greater than 1% by weight of the total weight of the composition.

5. The cosmetic composition according to claim 1, comprising the at least one liquid volatile linear alkane mixture in a total amount ranging from 0.5% to 90% by weight, relative to the total weight of the composition.

6. The cosmetic composition according to claim 1, wherein the weight ratio of the at least one liquid volatile linear alkane mixture to the at least one silicone copolymer has a value ranging from 2 to 100.

7. The cosmetic composition according to claim 1, further comprising at least one additional silicone compound chosen from polysiloxanes having a viscosity of more than 100 cSt.

8. The cosmetic composition according to claim 7, wherein the at least one additional polysiloxanes having a viscosity of more than 100 cSt is chosen from polydimethylsiloxane oils and silicone resins.

9. The cosmetic composition according to claim 1, further comprising at least one pigment.

10. The cosmetic composition according to claim 1, which is in anhydrous form.

11. A cosmetic method of treating keratin fibers, comprising applying a cosmetic composition to the keratin fibers, and optionally drying the keratin fibers at a temperature of greater than 40° C., wherein the cosmetic composition comprises at least one silicone copolymer based on at least one silicone resin and at least one fluid silicone; and at least one liquid volatile linear alkane mixture chosen from a mixture of n-undecane/n-tridecane (C11/C13);
wherein the weight ratio of the at least one liquid volatile linear alkane mixture to the at least one silicone copolymer has a value greater than or equal to 2; and
wherein the C11 volatile linear alkane, n-undecane, is present in an amount ranging from about 55% to about 80% by weight, and the C13 volatile linear alkane, n-tridecane, is present in an amount ranging from about 20% to about 45% by weight, relative to the total weight of the n-undecane/n-tridecane (C11/C13) mixture.

* * * * *